US009539286B2

(12) United States Patent
Bhat et al.

(10) Patent No.: US 9,539,286 B2
(45) Date of Patent: *Jan. 10, 2017

(54) BONE GRAFTS INCLUDING OSTEOGENIC STEM CELLS, AND METHODS RELATING TO THE SAME

(71) Applicant: Globus Medical, Inc., Audubon, PA (US)

(72) Inventors: Archana Bhat, Royersford, PA (US); Shairali Rao, Austin, TX (US); Daniel Laskowitz, Lancaster, PA (US)

(73) Assignee: Globus Medical, Inc., Audubon, PA (US)

( * ) Notice: Subject to any disclaimer, the term of this patent is extended or adjusted under 35 U.S.C. 154(b) by 140 days.

This patent is subject to a terminal disclaimer.

(21) Appl. No.: 14/057,806

(22) Filed: Oct. 18, 2013

(65) Prior Publication Data

US 2015/0110747 A1    Apr. 23, 2015

(51) Int. Cl.
| | | |
|---|---|---|
| *A61K 35/28* | (2015.01) | |
| *A61L 27/38* | (2006.01) | |
| *A61L 27/36* | (2006.01) | |
| *A61K 35/32* | (2015.01) | |
| *C12N 5/077* | (2010.01) | |
| *C12N 5/0775* | (2010.01) | |

(52) U.S. Cl.
CPC .............. *A61K 35/28* (2013.01); *A61K 35/32* (2013.01); *A61L 27/365* (2013.01); *A61L 27/3608* (2013.01); *A61L 27/3834* (2013.01); *A61L 27/3847* (2013.01); *C12N 5/0654* (2013.01); *C12N 5/0663* (2013.01); *A61L 2430/02* (2013.01); *C12N 2533/14* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 4,437,191 A | 3/1984 | van der Zel et al. | |
| 5,231,169 A | 7/1993 | Constantz | |
| 5,681,872 A | 10/1997 | Erbe | |
| 5,700,289 A | 12/1997 | Breitbart et al. | |
| 5,776,193 A | 7/1998 | Kwan et al. | |
| 5,854,207 A | 12/1998 | Lee et al. | |
| 5,914,356 A | 6/1999 | Erbe | |
| 5,939,039 A | 8/1999 | Sapieszko et al. | |
| 6,123,731 A | 9/2000 | Boyce et al. | |
| 6,264,701 B1 | 7/2001 | Brekke | |
| 6,294,041 B1 | 9/2001 | Boyce et al. | |
| 6,309,659 B1 | 10/2001 | Clokie | |
| 6,350,283 B1 | 2/2002 | Michelson | |
| 6,372,257 B1 | 4/2002 | Marchosky | |
| 6,432,436 B1 | 8/2002 | Gertzman et al. | |
| 6,437,018 B1 | 8/2002 | Gertzman et al. | |
| 6,458,375 B1 * | 10/2002 | Gertzman et al. | ............ 424/423 |
| 6,666,890 B2 | 12/2003 | Michelson | |
| 6,696,073 B2 | 2/2004 | Boyce et al. | |
| 6,706,067 B2 | 3/2004 | Shimp et al. | |
| 6,723,131 B2 | 4/2004 | Muschler | |
| 6,749,636 B2 | 6/2004 | Michelson | |
| 6,752,831 B2 | 6/2004 | Sybert et al. | |
| 6,776,800 B2 | 8/2004 | Boyer, II et al. | |
| 6,808,585 B2 | 10/2004 | Boyce et al. | |
| 6,843,807 B1 | 1/2005 | Boyce et al. | |
| 6,919,308 B2 | 7/2005 | Oppermann et al. | |
| 6,949,251 B2 | 9/2005 | Dalal et al. | |
| 7,022,137 B2 | 4/2006 | Michelson | |
| 7,041,641 B2 | 5/2006 | Rueger et al. | |
| 7,132,110 B2 | 11/2006 | Kay et al. | |
| 7,156,880 B2 | 1/2007 | Evans et al. | |
| 7,166,133 B2 | 1/2007 | Evans et al. | |
| 7,175,858 B2 | 2/2007 | Constantz et al. | |
| 7,235,107 B2 | 6/2007 | Evans et al. | |
| 7,262,003 B2 | 8/2007 | Kumar et al. | |
| 7,275,933 B2 | 10/2007 | Jia et al. | |
| 7,291,345 B2 | 11/2007 | Winterbottom et al. | |

(Continued)

FOREIGN PATENT DOCUMENTS

| | | |
|---|---|---|
| CA | 1341610 C | 4/1989 |
| CA | 2027259 C | 12/2000 |

(Continued)

OTHER PUBLICATIONS

Sakaguchi, Yusuke, et al. "Suspended cells from trabecular bone by collagenase digestion become virtually identical to mesenchymal stem cells obtained from marrow aspirates." Blood 104.9 (2004): 2728-2735.*

Kern, Susanne, et al. "Comparative analysis of mesenchymal stem cells from bone marrow, umbilical cord blood, or adipose tissue." Stem cells 24.5 (2006): 1294-1301.*

Lode, Anja, Anne Bernhardt, and Michael Gelinsky. "Cultivation of human bone marrow stromal cells on three-dimensional scaffolds of mineralized collagen: influence of seeding density on colonization, proliferation and osteogenic differentiation." Journal of tissue engineering and regenerative medicine 2.7 (2008): 400-407.*

(Continued)

*Primary Examiner* — Robert Yamasaki

(57) ABSTRACT

Bone grafts and constructs including stem cells are provided. Example bone grafts include osteogenic stem cells seeded on a scaffold of osteoconductive cortico-cancellous chips and/or osteoinductive demineralized bone. Example constructs include extracellular matrix on a synthetic scaffold, in which the ECM is secreted from MSCs seeded onto the synthetic scaffold. Also provided are methods of making the present bone grafts and scaffolds. Further provided are methods of promoting bone healing and treating wound healing, by administering the present bone grafts and constructs to a mammal in need thereof. Also provided are kits that include the present bone grafts and/or constructs, or components thereof.

18 Claims, No Drawings

(56) References Cited

U.S. PATENT DOCUMENTS

| | | |
|---|---|---|
| 7,332,452 B2 | 2/2008 | Ogawa et al. |
| 7,390,498 B2 | 6/2008 | Dalal et al. |
| 7,393,405 B2 | 7/2008 | Bohner |
| 7,473,678 B2 | 1/2009 | Lynch |
| 7,494,950 B2 | 2/2009 | Armitage et al. |
| 7,498,041 B2 | 3/2009 | Masinaei et al. |
| 7,517,489 B2 | 4/2009 | Akash |
| 7,582,309 B2 | 9/2009 | Rosenberg et al. |
| 7,611,536 B2 | 11/2009 | Michelson |
| 7,723,395 B2 | 5/2010 | Ringeisen et al. |
| 7,744,597 B2 | 6/2010 | Gaskins et al. |
| 7,776,100 B2 | 8/2010 | Brekke et al. |
| 7,785,634 B2 | 8/2010 | Borden |
| 7,811,608 B2 | 10/2010 | Kay et al. |
| 7,824,702 B2 | 11/2010 | Wironen et al. |
| 7,833,278 B2 | 11/2010 | Evans et al. |
| 7,887,598 B2 | 2/2011 | Evans et al. |
| 7,892,291 B2 | 2/2011 | Evans et al. |
| 7,910,690 B2 | 3/2011 | Ringeisen et al. |
| 7,931,692 B2 | 4/2011 | Sybert et al. |
| 7,939,108 B2 | 5/2011 | Morris et al. |
| 7,942,961 B2 | 5/2011 | Asgary |
| 7,947,759 B2 | 5/2011 | Lin et al. |
| 7,959,941 B2 | 6/2011 | Knaack et al. |
| 7,977,094 B2 | 7/2011 | Masinaei et al. |
| 8,002,813 B2 | 8/2011 | Scarborough et al. |
| 8,067,078 B1 | 11/2011 | Espinosa et al. |
| 8,093,313 B2 | 1/2012 | Miller |
| 8,105,383 B2 | 1/2012 | Michelson |
| 8,137,403 B2 | 3/2012 | Michelson |
| 8,147,860 B2 | 4/2012 | Rosenberg et al. |
| 8,147,862 B2 | 4/2012 | McKay |
| 8,163,032 B2 | 4/2012 | Evans et al. |
| 8,188,229 B2 | 5/2012 | Ringeisen et al. |
| 8,197,474 B2 | 6/2012 | Scarborough et al. |
| 8,202,539 B2 | 6/2012 | Behnam et al. |
| 8,221,781 B2 | 7/2012 | Rosenberg et al. |
| 8,232,327 B2 | 7/2012 | Garigapati et al. |
| 8,268,008 B2 | 9/2012 | Betz et al. |
| 8,287,915 B2 | 10/2012 | Clineff et al. |
| 8,303,967 B2 | 11/2012 | Clineff et al. |
| 8,303,971 B2 | 11/2012 | Cieslik et al. |
| 8,309,106 B2 | 11/2012 | Masinaei et al. |
| 8,323,700 B2 | 12/2012 | Morris et al. |
| 8,328,876 B2 | 12/2012 | Behnam et al. |
| 8,333,985 B2 | 12/2012 | Knaack et al. |
| 8,357,384 B2 | 1/2013 | Behnam et al. |
| 8,394,141 B2 | 3/2013 | Mills et al. |
| 8,399,409 B2 | 3/2013 | Lynch et al. |
| 8,419,802 B2 | 4/2013 | Evans et al. |
| 8,425,619 B2 | 4/2013 | Evans et al. |
| 8,435,306 B2 | 5/2013 | Evans et al. |
| 8,435,343 B2 | 5/2013 | Yahav et al. |
| 8,435,566 B2 | 5/2013 | Behnam et al. |
| 8,454,988 B2 | 6/2013 | Rosenberg et al. |
| 8,460,686 B2 | 6/2013 | Clineff et al. |
| 8,475,824 B2 | 7/2013 | McKay |
| 8,506,981 B1 | 8/2013 | Borden |
| 8,506,985 B2 | 8/2013 | Garcia De Castro Andrews et al. |
| 8,524,265 B2 | 9/2013 | McKay |
| 8,529,962 B2 | 9/2013 | Morris et al. |
| 8,545,858 B2 | 10/2013 | Rosenberg et al. |
| 8,545,864 B2 | 10/2013 | Morris et al. |
| 8,551,519 B2 | 10/2013 | Bezwada |
| 8,551,525 B2 | 10/2013 | Cook et al. |
| 8,562,648 B2 | 10/2013 | Kaes et al. |
| 8,580,865 B2 | 11/2013 | Peters et al. |
| 8,597,675 B2 | 12/2013 | Murphy et al. |
| 8,613,938 B2 | 12/2013 | Akella et al. |
| 8,623,094 B2 | 1/2014 | Evans et al. |
| 8,641,774 B2 | 2/2014 | Rahaman et al. |
| 8,642,061 B2 | 2/2014 | Shimp et al. |
| 8,652,503 B2 | 2/2014 | Wironen et al. |
| 8,663,326 B2 | 3/2014 | Osman |
| 8,663,672 B2 | 3/2014 | Manrique et al. |
| 8,663,677 B2 | 3/2014 | Fu et al. |
| 8,685,429 B2 | 4/2014 | Koblish et al. |
| 8,734,525 B2 | 5/2014 | Behnam et al. |
| 8,740,987 B2 | 6/2014 | Geremakis et al. |
| 8,747,899 B2 | 6/2014 | Chaput et al. |
| 8,753,391 B2 | 6/2014 | Lu et al. |
| 8,753,689 B2 | 6/2014 | Morris et al. |
| 8,758,792 B2 | 6/2014 | Behnam et al. |
| 8,778,378 B2 | 7/2014 | Clineff et al. |
| 8,795,382 B2 | 8/2014 | Lin et al. |
| 8,802,626 B2 | 8/2014 | Rueger et al. |
| 8,834,928 B1 | 9/2014 | Truncale et al. |
| 8,864,843 B2 | 10/2014 | Lu et al. |
| 8,871,235 B2 | 10/2014 | Borden |
| 8,876,532 B2 | 11/2014 | Atkinson et al. |
| 8,877,221 B2 | 11/2014 | McKay |
| 8,883,210 B1 | 11/2014 | Truncale et al. |
| 8,926,710 B2 | 1/2015 | McKay |
| 8,992,964 B2 | 3/2015 | Shelby et al. |
| 8,992,965 B2 | 3/2015 | Behnam |
| 2001/0038848 A1 | 11/2001 | Donda et al. |
| 2002/0076429 A1 | 6/2002 | Wironen et al. |
| 2002/0098222 A1 | 7/2002 | Wironen et al. |
| 2002/0193883 A1 | 12/2002 | Wironen |
| 2002/0197242 A1 | 12/2002 | Gertzman |
| 2003/0009235 A1 | 1/2003 | Manrique et al. |
| 2003/0055512 A1 | 3/2003 | Genin et al. |
| 2003/0149437 A1 | 8/2003 | Livne et al. |
| 2004/0091462 A1 | 5/2004 | Lin et al. |
| 2005/0118230 A1 | 6/2005 | Hill et al. |
| 2005/0251267 A1 | 11/2005 | Winterbottom et al. |
| 2005/0281856 A1 | 12/2005 | McGlohorn et al. |
| 2006/0018942 A1 | 1/2006 | Rowe et al. |
| 2006/0036331 A1 | 2/2006 | Lu et al. |
| 2006/0147545 A1 | 7/2006 | Scarborough et al. |
| 2007/0083270 A1 | 4/2007 | Masinaei et al. |
| 2007/0098756 A1 | 5/2007 | Behnam |
| 2007/0105222 A1 | 5/2007 | Wolfinbarger et al. |
| 2007/0110820 A1 | 5/2007 | Behnam |
| 2007/0113951 A1 | 5/2007 | Huang |
| 2008/0033572 A1 | 2/2008 | D'Antonio et al. |
| 2008/0069852 A1 | 3/2008 | Shimp et al. |
| 2008/0091270 A1 | 4/2008 | Miller et al. |
| 2008/0124374 A1* | 5/2008 | Freyman ............... A61K 35/28 424/423 |
| 2008/0152687 A1 | 6/2008 | Thorne |
| 2008/0187571 A1 | 8/2008 | Clineff et al. |
| 2008/0262633 A1 | 10/2008 | Williams |
| 2009/0012625 A1 | 1/2009 | Ying et al. |
| 2009/0074753 A1 | 3/2009 | Lynch |
| 2009/0157087 A1 | 6/2009 | Wei et al. |
| 2009/0192474 A1 | 7/2009 | Wei et al. |
| 2009/0238853 A1 | 9/2009 | Liu |
| 2009/0312842 A1 | 12/2009 | Bursac et al. |
| 2009/0317447 A1 | 12/2009 | Hsiao et al. |
| 2010/0055078 A1 | 3/2010 | Hughes-Fulford |
| 2010/0098673 A1 | 4/2010 | D'Antonio |
| 2010/0119577 A1 | 5/2010 | Min |
| 2010/0124563 A1* | 5/2010 | Coleman et al. ............. 424/423 |
| 2010/0145469 A1 | 6/2010 | Barralet et al. |
| 2010/0196333 A1 | 8/2010 | Gaskins et al. |
| 2010/0203155 A1 | 8/2010 | Wei et al. |
| 2010/0234966 A1 | 9/2010 | Lo |
| 2011/0045044 A1 | 2/2011 | Masinaei et al. |
| 2011/0066242 A1 | 3/2011 | Lu et al. |
| 2011/0070312 A1 | 3/2011 | Wei et al. |
| 2011/0117018 A1 | 5/2011 | Hart et al. |
| 2011/0117165 A1 | 5/2011 | Melican et al. |
| 2011/0117166 A1 | 5/2011 | Melican |
| 2011/0117171 A1 | 5/2011 | Melican et al. |
| 2011/0144764 A1 | 6/2011 | Bagga et al. |
| 2011/0224675 A1 | 9/2011 | Tofighi et al. |
| 2011/0262554 A1 | 10/2011 | Masinaei et al. |
| 2011/0276147 A1 | 11/2011 | Cook et al. |
| 2011/0280924 A1 | 11/2011 | Lin et al. |
| 2012/0053692 A1 | 3/2012 | Voor et al. |
| 2012/0064290 A1 | 3/2012 | Esat et al. |
| 2012/0093895 A1 | 4/2012 | Song et al. |
| 2012/0164187 A1 | 6/2012 | Ollila et al. |

(56) References Cited

U.S. PATENT DOCUMENTS

| | | |
|---|---|---|
| 2012/0207839 A1 | 8/2012 | Liu |
| 2012/0237568 A1 | 9/2012 | Murphy et al. |
| 2013/0013071 A1 | 1/2013 | Betz et al. |
| 2013/0059382 A1 | 3/2013 | Tsai et al. |
| 2013/0084636 A1 | 4/2013 | Cho |
| 2013/0122057 A1 | 5/2013 | Garigapati et al. |
| 2013/0144376 A1 | 6/2013 | Dave et al. |
| 2013/0145963 A1 | 6/2013 | Cai et al. |
| 2013/0150227 A1 | 6/2013 | Wang et al. |
| 2013/0189338 A1 | 7/2013 | Drapeau et al. |
| 2013/0195805 A1 | 8/2013 | Wei et al. |
| 2013/0202670 A1 | 8/2013 | Darmoc et al. |
| 2013/0236513 A1 | 9/2013 | Guelcher et al. |
| 2013/0244942 A1 | 9/2013 | Benedict et al. |
| 2013/0274890 A1 | 10/2013 | McKay |
| 2013/0282138 A1 | 10/2013 | McKay |
| 2013/0297038 A1 | 11/2013 | McKay |
| 2014/0010890 A1 | 1/2014 | Borden |
| 2014/0031950 A1 | 1/2014 | Cook et al. |
| 2014/0079753 A1 | 3/2014 | Darby et al. |
| 2014/0170202 A1 | 6/2014 | Peters et al. |
| 2014/0195005 A1 | 7/2014 | McKay |
| 2014/0205674 A1 | 7/2014 | Wei |
| 2014/0212471 A1 | 7/2014 | Drapeau et al. |
| 2014/0222159 A1 | 8/2014 | Bursac et al. |
| 2014/0271779 A1 | 9/2014 | Bagga et al. |
| 2014/0271786 A1 | 9/2014 | Bagga et al. |
| 2014/0271914 A1 | 9/2014 | Wagner |
| 2014/0294913 A1 | 10/2014 | Hasirci et al. |
| 2014/0314822 A1 | 10/2014 | Carter et al. |
| 2015/0010607 A1 | 1/2015 | Francis et al. |

FOREIGN PATENT DOCUMENTS

| | | |
|---|---|---|
| WO | 2005070328 A1 | 8/2005 |
| WO | 2005084701 A1 | 9/2005 |
| WO | 2008019024 | 2/2008 |
| WO | 2010051032 A1 | 5/2010 |
| WO | 2010139792 | 12/2010 |
| WO | 2014128289 A1 | 8/2014 |

OTHER PUBLICATIONS

Bosnakovski, Darko, et al. "Isolation and multilineage differentiation of bovine bone marrow mesenchymal stem cells." Cell and tissue research 319.2 (2005): 243-253.*

* cited by examiner

BONE GRAFTS INCLUDING OSTEOGENIC STEM CELLS, AND METHODS RELATING TO THE SAME

TECHNICAL FIELD

The present invention relates generally to bone and wound healing using bone grafts and constructs that include stem cells. The invention relates to the bone grafts and constructs themselves. The invention also relates to methods of making the present bone grafts and constructs and methods of promoting bone or wound healing in a mammal by administering the present bone grafts and/or constructs to the mammal. The invention further relates to kits that include one or more of the present bone grafts or constructs, or components thereof.

BACKGROUND

Bone grafting is a surgical procedure that replaces missing bone and/or repairs bone fractures. Bone generally has the ability to regenerate well but may require a scaffold to do so. Bone grafts may be allograft (cadaveric bone e.g., from a bone bank), autologous (i.e., bone harvested from the patient's own body, for example from the iliac crest), or synthetic. Most bone grafts are expected to be resorbed and replaced as the natural bone heals over time.

Successful bone grafts may include osteoconduction (guiding the reparative growth of the natural bone), osteoinduction (encouraging undifferentiated cells to become active osteoblasts), and osteogenesis (living bone cells in the graft material contributing to bone remodeling). Bone grafts are osteogenic if they contain viable cells that are capable of bone regeneration, which is advantageous for bone healing. Osteogenesis occurs with autografts. Autografts are considered osteogenic because they contain a high number of bone forming cells. However, autographs have certain drawbacks in that there is limited availability of autographs, and autographs may result in donor site morbidity.

SUMMARY

There is a need in the art for bone grafts and constructs that are osteogenic, osteoinductive and/or osteoconductive without the drawbacks of present autograph products.

The present invention is related to the development of suitable bone grafts or constructs that contain stem cells on a scaffold. In addition to stem cells, they may include for example, a mix of osteoinductive demineralized bone and osteoconductive cortico-cancellous chips, to promote bone healing. Examples of the present invention provide bone grafts that are osteogenic, osteoinductive and osteoconductive. In addition, according to non-limiting example embodiments, the osteogenic cells may be isolated from bone marrow harvested from the iliac crest, or they may be isolated from adipose tissue, or from long bones such as femur, tibia, humerus, etc. According to example embodiments, a final product bone graft product may include DBM (demineralized bone), osteogenic stem cells, and cortico-cancellous chips.

The present invention also relates to constructs that include stem cells seeded on a synthetic scaffold. The stem cells are then instructed using chemical cues to undergo osteogenic differentiation. This causes the MSCs to secret extracellular matrix (ECM). The extracellular matrix (ECM) plays an important role in regulating cell behavior. A decellularized tissue matrix provides a complex ECM-based scaffold, similar to native tissue. Current products provide a decellularized matrix that is derived from skin, and use this as a scaffold for cell attachment and is used to promote wound healing. However, having ECM on synthetic scaffolds helps combine the properties of the synthetic scaffold and the unique properties of the ECM, and together help modulate the healing process. Having the ECM on a suitable synthetic scaffold provides better mechanical properties in addition to providing the cues similar to that of native tissue.

The present inventors have developed unique biomaterials that combine the properties of the scaffold and an osteoinductive and osteoconductive cell derived ECM that directs cell fate and drives bone healing.

Also provided are methods of making the present bone grafts and constructs and methods of promoting bone and wound healing by using such bone grafts and/or constructs.

Further provided are kits that include one or more of the present bone grafts and/or constructs, as well as kits that include components for making the same.

DETAILED DESCRIPTION

The present invention relates generally to bone grafts and constructs that include stem cells. The invention also relates to methods of making the present bone grafts and constructs and methods of promoting bone or wound healing in a mammal by administering the present bone grafts and/or constructs to the mammal. The invention further relates to kits that include such bone grafts and/or constructs, or components thereof.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. As used herein, unless otherwise required by context, singular terms include pluralities and plural terms include the singular.

As used herein, "extracellular matrix," or "ECM" is the extracellular component consisting of an intricate network of proteins and polysaccharides that are secreted by the cells and play an important role in cell-cell signaling. Mesenchymal Stem Cells (MSCs) generate ECMs in vivo as they differentiate in different cell types. However, MSCs may be made to secrete the ECM ex vivo, by providing chemical cues that would facilitate differentiation of the MSCs.

As indicated herein, bone grafts are provided herein that include a scaffold that includes at least one of osteoinductive demineralized bone and/or osteoconductive cortico-cancellous chips; and osteogenic stem cells. According to more specific non-limiting example embodiments, bone grafts are provided that include osteogenic stem cells in a mix of osteoinductive demineralized bone and osteoconductive cortico-cancellous chips to promote bone healing.

According to non-limiting example embodiments, the present bone grafts may be made by methods that include seeding osteogenic cells onto a tissue culture substrate, such as a flask and allowing the cells to attach; washing the substrate to remove blood cells; detaching osteogenic stem cells from the substrate; and seeding the osteogenic stem cells on a scaffold comprising at least one of osteoinductive demineralized bone and osteoconductive cortico-cancellous chips.

According to non-limiting example embodiments, the osteogenic stem cells may be obtained by treating cancellous bone from e.g., a femur or tibia with collagenase and separating loosely attached cells by centrifugation.

The cortico-cancellous chips may be obtained for example, from the condyles from fresh frozen bone. In particular, the condyles may be separated from the cortical shaft, and sectioned into smaller pieces. The decellularized condyles may be milled to form cortico-cancellous chips.

The cortical bone may be milled and demineralized in HCl to form demineralized bone (DBM). As used herein, the terms "demineralized bone", "demineralized bone matrix", and "DBM" are used interchangeably herein.

Thus, according to example embodiments, cortical bone may be treated and processed to form DBM. The DBM and/or cortico cancellous chips (which be obtained for example from condyles), may be used individually or as a mix or other combination together to form the scaffold.

The bone marrow from the cortical shaft may be flushed and mixed with the centrifuged stem cells (e.g., obtained from cancellous bone). The mixture of cells may be seeded onto a tissue culture flask or other tissue culture substrate and allowed to attach thereto.

The substrate may then be washed to remove any blood cells, and the bone forming cells will be detached e.g., using trypsin. These cells will then be seeded on the scaffold of cortico-cancellous chips, demineralized bone, or a mix or other combination of the same.

According to alternative embodiments, the isolated osteogenic stem cells (obtained e.g. after treating the cancellous bone from the febur or tibia with collagenase), may be seeded directly on a scaffold including DBM, CC, or a mix or other combination of the same.

Thus, provided herein are methods of making bone grafts that include seeding osteogenic cells on a scaffold; which scaffold includes osteoinductive demineralized bone and/or osteoconductive cortico-cancellous chips. According to non-limiting example embodiments, the present methods may further include rinsing the scaffold in phosphate buffered saline (PBS) to remove unwanted cells, preferably all unwanted cells, or as many as possible.

In accordance with any of these embodiments, the osteogenic cells may include e.g., osteogenic cells isolated from bone marrow harvested from iliac crest, or from long bones such as femur, tibia, humerus etc. Thus, example embodiments may include bone grafts that include osteogenic cells isolated from bone marrow harvested from iliac crest, or from long bones such as femur, tibia, humerus etc. which are seeded directly on the scaffold of CC, DBM, or a mixture thereof. Following cell attachment, the scaffolds may be rinsed e.g., with PBS to remove unwanted cells. Thus, the stem cells in these embodiments may be from the same donor from which the DBM and CC are derived.

According to other non-limiting example embodiments, the osteogenic cells may include e.g., osteogenic cells isolated from adipose tissue. The adipose tissue may be sectioned and treated with collagenase enzyme. The tissue may then be either centrifuged to facilitate cell separation or incubated at 37° C. in a petri dish to facilitate cell migration from the tissue onto the petri dish. Thus, example embodiments may include bone grafts that include osteogenic cells isolated from adipose tissue, which are seeded directly on the scaffold of CC, DBM, or a mixture thereof. Following cell attachment, the scaffolds may be rinsed to remove unwanted cells.

According to non-limiting example embodiments, the scaffold is a mix of demineralized bone matrix and cortico-cancellous chips in a ratio of about 1:1-1:3, or any point there-between, including for example, ratios of about 1:1, 1:2 or 1:3.

According to further example embodiments, the osteogenic stem cells may be present in the bone graft in an amount of at least 20,000 cells/cc of total bone graft. The bone graft may be for example, in a semi-solid state, such as in a putty-like state.

In any of the above embodiments, the final products may be stored at −80° C. or −180° C.

Further provided herein are methods of promoting bone healing, which include administering to a mammal in need thereof, a bone graft that includes osteogenic stem cells and a scaffold that includes osteoinductive demineralized bone and/or osteoconductive cortico-cancellous chips.

Also provided herein, according to non-limiting example embodiments, are constructs that include ECM on synthetic scaffolds. In these embodiments, Mesenchymal stem cells (MSCs) are seeded onto a synthetic scaffold to form the construct. The stem cells are then instructed using chemical cues to undergo osteogenic differentiation. This causes the MSCs to secrete the extracellular matrix onto synthetic scaffolds. As used herein, the terms "Mesenchymal stem cells" and "MSC" are used interchangeably. According to non-limiting example embodiments, the MSCs are isolated from adipose tissue, bone marrow or bone. According to example embodiments, the mesenchymal stem cells (MSCs) are derived from bone marrow or cancellous bone. The MSCs may be human or bovine derived. The MSCs in these construct embodiments may be purchased.

According to non-limiting example embodiments, the synthetic scaffold may include natural or synthetic materials, such as at least one of collagen-ceramic, collagen-bioglass, or PLGA. By way of non-limiting example embodiment, the scaffolds may include collagen-ceramic, collagen-bioglass, or PLGA-based scaffolds. Other suitable biocompatible scaffolds are also contemplated however.

According to non-limiting example embodiments, the present constructs may have a seeding density of from 20,000 to 100,000 cells/cm$^2$ of the growth surface area on which the cells are seeded.

According to non-limiting example embodiments, the mesenchymal stem cells in the construct are cultured in media; and the construct is rinsed in PBS, treated with DNAse, and air dried.

Also included herein are methods of making constructs that include seeding mesenchymal stem cells (MSCs) on a synthetic scaffold to form a construct; culturing the MSCs in supplemented media; rinsing the construct with PBS and treating with DNAse; rinsing the construct with PBS to remove prior reagents; and air drying the construct.

The culturing may include for example, culturing for 5-15 days in supplemented media, which may be for example, α-MEM, 10% fetal bovine serum, 1% penicillin-streptomycin, 50 μg/ml ascorbic 2 phosphate). The culture media may be changed every 2-3 days with fresh media.

According to example embodiments, at the end of the culture period the construct is rinsed with PBS. After such rinsing, the construct may be treated with PBS containing 0.1-2% tritonX-100 and 10-40 mM $NH_4OH$ for 5-30 minutes, or according to other example embodiments for 5-10 minutes, before further rinsing with PBS and treatment with DNAase. According to further example embodiments, the construct is treated with PBS containing 0.3-1% tritonX-100 and 10-30 mM $NH_4OH$. According to further non-limiting example embodiments, the construct is treated with PBS containing 0.5% tritonX-100 and 20 mM $NH_4OH$.

According to other example embodiments, at the end of the culture period the construct is rinsed with PBS; and thereafter, the construct may be further processed through 2-3 freeze thaw cycles before further rinsing with PBS and treatment with DNAase.

The treatment of the construct with DNAse may include treatment of DNAase in a concentration of 100-300 units/ml, or of approximately 150 units/ml, for approximately (0-60 min) at about 37° C., e.g., under standard tissue culture condition. Treatment with DNAse may be followed by 2-3 rinses in PBS for removal of prior reagents, preferably of all prior reagents.

According to example embodiments, the construct may then be air dried and stored on the shelf.

Also provided herein are methods of making a construct comprising seeding mesenchymal stem cells (MSCs) onto a synthetic scaffold; culturing the cells in cell culture media; and replacing the cell culture media with freezing media that contains DMSO (e.g., about 10%), and freezing. In these embodiments, the constructs may be seeded with allogenic mesenchymal stem cells isolated from humans. The seeding density may be 20,000-100,000 cells/$cm^2$. The cell culture media may be replaced e.g., after about 24 hours of attachment. The cell-based constructs may be stored for example at about −80° C. (e.g., about negative 78° C. to −82° C.) or vapour phase liquid nitrogen.

The constructs may be for example, in solid or putty form.

Further provided are methods of treatment for wound healing that include administering to a mammal in need thereof any of the present constructs, including e.g., ECM.

Non-limiting example embodiments also include kits that include one or more of the present bone grafts and/or constructs and optionally instructions for preparing such constructs or bone grafts and/or for using them for bone healing or wound healing.

Further example embodiments are directed to kits that include components for making the present bone grafts and/or constructs, including for example, synthetic scaffolds, cell culture media, PBS, cortico-cancellous chips, demineralized bone, a tissue culture substrate such as a flask, trypsin, or mixtures or other combinations thereof. Additional components, instructions and/or apparatus' may also be included.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

In this example, a bone graft is formed in accordance with the present invention. Condyles from fresh frozen bone may be separated from the cortical shaft, and sectioned into smaller pieces. The osteogenic cells in this example may be obtained after treating the cancellous bone from the femur or tibia with collagenase. The loosely attached cells may then be separated by centrifugation. The decellularized condyles may be milled to form cortico-cancellous chips (CC). The bone marrow from the cortical shaft may be flushed and mixed in with the centrifuged cells.

The mixture of bone marrow and osteogenic cells may be seeded onto a tissue culture substrate such as a flask and allowed to attach. The substrate may be washed to remove any blood cells, and the bone forming cells detached using trypsin.

The cortical bone may be milled and demineralized e.g., in HCl to form DBM. The DBM may then be mixed with cortico-cancellous chips. The cells may then be seeded on the scaffold which could be CC, DBM, or a mix or other combination of CC and DBM to form a bone graft.

Example 2

In this example, the osteogenic cells (isolated as set forth in Example 1) may be seeded directly on the scaffold, which could be DBM, CC, or a mix of DBM and CC. After osteogenic cell attachment, the scaffolds may be rinsed in phosphate buffered saline (PBS) to remove all unwanted cells.

Example 3

In this example, the osteogenic cells are isolated from bone marrow harvested from the iliac crest. The harvested bone marrow may then be seeded directly on the scaffold (CC, DBM, or a mix of CC and DBM). Following cell attachment, the scaffolds may be rinsed to remove unwanted cells.

Example 4

In this example, the osteogenic cells are isolated from adipose tissue. The adipose tissue may be sectioned and treated with collagenase enzyme. The tissue may then be either centrifuged to facilitate cell separation or incubated at 37° C. in a petri dish to facilitate cell migration from the tissue onto the petri dish. The isolated cells may then be seeded on the scaffold (e.g., CC chips, DBM, or mix or other combination of CC chips and DBM).

Example 5

In this example, a construct is prepared in accordance with embodiments of the present composition is prepared. Mesenchymal stem cells (MSCs) either derived from bone marrow or cancellous bone are seeded onto collagen-ceramic scaffold. The MSCs may be human or bovine derived. The seeding density may be 20,000-100,000 cells/$cm^2$. The cells are cultured for 5-15 days in supplemental media (α-MEM, 10% fetal bovine serum, 1% penicillin-streptomycin, 50 μg/ml ascorbic 2 phosphate). The culture media is changed every 2-3 days with fresh media. At the end of the culture period, the construct may be rinsed with PBS and treated with PBS containing 0.5% triton-100 and 20 mM $NH_4OH$, for 5-10 min. At the end of the treatment the constructs are rinsed in PBS and treated with DNAse (150 units/ml) for 1 hour at 37° C. This treatment will be followed by 2-3 rinses in PBS to confirm complete removal of all prior reagents. The construct may then be air dried and stored on the shelf.

Example 6

In this example, Mesenchymal stem cells (MSCs) either derived from bone marrow or cancellous bone are seeded onto a collagen-ceramic scaffold. The MSCs may be human or bovine derived. The seeding density may be 20,000-100,000 cells/cm². The cells are cultured for 5-15 days in supplemented media (α-MEM, 10% fetal bovine serum, 1% penicillin-streptomycin, 50 μg/ml ascorbic 2 phosphate). The culture media may be changed every 2-3 days with fresh media. At the end of the culture period, the construct is rinsed with PBS and processed through 2-3 freeze thaw cycles. A freeze thaw cycle includes freezing constructs in liquid nitrogen for 3-5 min, thawing at 37° C. water bath for 5 min, and rinsing constructs in PBS. At the end of the treatment the constructs are rinsed in PBS and treated with DNAse (150 units/ml) for 1 hr at 37° C. This treatment will be followed by 2-3 rinses in PBS to confirm removal of all prior reagents. The construct may then be air dried and stored on the shelf.

Example 7

In this example, the constructs from Examples 5 and 6 may be seeded with allogenic mesenchymal stem cells isolated from humans. The seeding density may be 20,000-100,000 cells/cm². After 24 hr of attachment the cell culture media may be replaced with freezing media that contains 10% DMSO, and frozen. The cell based constructs may be stored at −80° C. or vapour phase liquid nitrogen.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of making a bone graft comprising:
   obtaining bone including condyles, cortical bone, cancellous bone, and bone marrow from a donor;
   culturing osteogenic stem cells from the cancellous bone, bone marrow, or both by seeding cells onto a tissue culture substrate, allowing the cells to attach, washing the substrate to remove blood cells, and detaching osteogenic stem cells from the substrate;
   seeding the osteogenic stem cells on a scaffold consisting of osteoinductive demineralized bone obtained from the cortical bone and osteoconductive cortico-cancellous chips obtained from the condyles to form the bone graft,
   wherein the osteogenic stem cells, demineralized bone, and cortico-cancellous chips are derived from the same donor.

2. The method of claim 1, wherein the osteogenic stem cells are obtained by treating cancellous bone from a femur or tibia with collagenase and separating loosely attached cells by centrifugation.

3. The method of claim 1, wherein the osteogenic stem cells comprise osteogenic cells isolated from bone marrow harvested from an iliac crest.

4. The method of claim 1, wherein the osteogenic stem cells comprise osteogenic cells isolated from adipose tissue.

5. The method of claim 1, further comprising rinsing the scaffold in phosphate buffered saline to remove unwanted cells.

6. The method of claim 1, wherein the scaffold is a mix of demineralized bone and cortico-cancellous chips in a ratio of about 1:1, 1:2 or 1:3.

7. The method of claim 1, wherein the osteogenic stem cells are seeded on the scaffold such that the bone graft has a seeding density of 20,000 to 100,000 cells/cm².

8. The method of claim 1, wherein the osteogenic stem cells are mesenchymal stem cells.

9. The method of claim 8, wherein the mesenchymal stem cells are derived from a human source.

10. The method of claim 8, wherein the mesenchymal stem cells are derived from a bovine source.

11. The method of claim 8, wherein the bone graft has a putty-like consistency.

12. A method of making a bone graft having viable cells, the method comprising:
    obtaining bone including condyles, cortical shaft, cancellous bone, and bone marrow;
    separating the condyles from the cortical shaft and cancellous bone;
    treating the cancellous bone with collagenase and separating loose cells by centrifugation;
    flushing the bone marrow from the cortical shaft and mixing the bone marrow with the loose cells separated by centrifugation to form a mixture of bone marrow and cells;
    culturing the mixture of bone marrow and cells on a tissue culture substrate and obtaining osteogenic stem cells;
    milling the condyles to form cortico-cancellous chips;
    milling and demineralizing the cortical shaft to form demineralized bone matrix;
    combining the cortico-cancellous chips and demineralized bone matrix to form a scaffold; and
    seeding the osteogenic stem cells on the scaffold to form the bone graft having viable cells capable of bone regeneration.

13. The method of claim 12, wherein the scaffold consists of a mixture of demineralized bone matrix and cortico-cancellous chips in a ratio of about 1:1.

14. The method of claim 12, wherein the bone is a long bone including one or more of a femur, tibia, and humerus.

15. The method of claim 12, wherein the osteogenic stem cells are seeded on the scaffold such that the bone graft has a seeding density of 20,000 to 100,000 cells/cm².

16. The method of claim 12, wherein the osteogenic stem cells are mesenchymal stem cells.

17. The method of claim 16, wherein the mesenchymal stem cells are derived from a human source.

18. The method of claim 12, wherein the bone graft has a putty-like consistency.

* * * * *